(12) United States Patent
Putman (10) Patent No.: US 6,775,004 B1
(45) Date of Patent: Aug. 10, 2004

(54) MEASURING SURFACE ROUGHNESS TO CALCULATE FILLER DISPERSION IN A POLYMER SAMPLE

(76) Inventor: John B. Putman, 1810 Highbridge Rd., Cuyahoga Falls, OH (US) 44223

(*) Notice: Subject to any disclaimer, the term of this patent is extended or adjusted under 35 U.S.C. 154(b) by 0 days.

(21) Appl. No.: 10/266,411

(22) Filed: Oct. 8, 2002

(51) Int. Cl.$^7$ .......................... G01N 21/55; G01B 11/30
(52) U.S. Cl. ........................................ 356/445; 356/600
(58) Field of Search ................................ 356/445–448, 356/600

(56) References Cited

U.S. PATENT DOCUMENTS

| | | | | |
|---|---|---|---|---|
| 4,220,042 A | | 9/1980 | Vegvari et al. | ........... 73/150 R |
| 4,699,516 A | * | 10/1987 | Bartz et al. | .................. 356/445 |
| 5,974,167 A | * | 10/1999 | Reszler | ........................ 382/141 |

OTHER PUBLICATIONS

A.I. Medalia, Rubber Chem. and Technology, 34 pp. 1134–1140 (1960).
ASTM D2663–95a, "Standard Test Methods for Carbon Black—Dispersion", 09–10, American Society for Testing and Matetrials, West conshocken, PA, pp. 401–411 (2001).
A.Y. Coran and J.B. Donnet, Rubber Chem. and Technology, 65 pp. 973–997 (1992).
C.H. Leigh–Dugmore, Rubber Chem. and Technology, 29, pp. 1301–1308 (1956).
ISO 11345, "Rubber—Asssessment of Carbon Black Dispersion—Rapid Comparative Method", (1997).
L. Anderson, J. Sunder, S. Persson and L. Nilsson, Rubber World, Mar. 1999, p. 36.
M. Gerspacher and C.P. O'Farrell, Paper No. E, 161th Spring Technical Meeting Rubber Division, American Chemical Society, Savannah, GA, Apr. 2002.
N. A. Stumpe, Jr. and H.E. Railsback, Rubber World, 151(3), p. 41, (1964).
P.C. Vegvari, W. M. Hess and V. E. Chirico, Rubber Chem. and technology, 51, pp. 817–839, (1978).
P. Lovgren and S. Persson, Tire Technology International (1994).
S. Persson, European Rubber Journal, Nov. p. 28 (1978).
W.M. Hess and F. P. Ford, Rubber Chem. Technology 5, 1175 (1963).
W.M. Hess, Rubber Chem. Technology, 64, p. 386, (1991).
B.R. Richmond, Paper No. 68, The Spring Technical Meeting, Rubber Divison, Am. Chem. Soc., Denver, CO, May 1993.

* cited by examiner

*Primary Examiner*—Frank G. Font
*Assistant Examiner*—Amanda Merlino
(74) *Attorney, Agent, or Firm*—Renner, Kenner, Greive, Bobak, Taylor & Weber (57) ABSTRACT

This invention contemplates the preparation of a cut surface of a polymer compounded with fillers, while leaving dispersed filler agglomerates substantially undisturbed and apparent from surface disturbances (in the form of depressions or bumps), which represent the presence of such agglomerates. The areas of these surface disturbances that exceed a selected threshold are then summed, and that summation is indicative of undispersed filler in the sample plane. The percent of the summation area to the total area of the plane is then indicative of the percent of undispersed filler, which can be employed to calculate a dispersion rating (%) from the known volume percent of the filler in the compounded polymer under study.

3 Claims, 4 Drawing Sheets

MEASURING SURFACE ROUGHNESS TO CALCULATE FILLER DISPERSION IN A POLYMER SAMPLE

BACKGROUND OF THE INVENTION

The present invention generally relates to a method for measuring filler dispersion in a polymer sample, and, more particularly, relates to a method for quantifying filler dispersion in a polymer sample through the manipulation of data obtained from a reflected light measurement method for analyzing filler dispersion.

The physical properties of polymer products containing reinforcing fillers are generally dependent upon not only the nature of the polymer itself, but also the quality and uniformity of the dispersion of the fillers within the polymer matrix. Typically, the polymers and fillers and any other selected ingredients are first mixed together in a "masterbatch" to produce a uniformly blended compound, in preparation for a second or final pass, in which accelerators and curing agents are added so that the compounded polymer may be vulcanized as a final product. Generally, the individual filler particles exhibit a natural cohesiveness for each other, and it is the objective of processing to overcome this cohesiveness and to disperse the fillers into the polymer to as near the individual aggregate size as possible. Depending upon the application, the dispersion of the filler may be considered to be adequate when a given percentage of the agglomerates (clusters of filler aggregates) are of a size or diameter below a predetermined magnitude. For example, when dispersing carbon black fillers into rubber, in many applications the dispersion will be considered to be adequate when 95% of the agglomerates are below 10 microns in diameter.

Thus, dispersion is concerned with causing these agglomerates to separate and become uniformly scattered throughout the polymeric matrix. The degree of dispersion is the fineness of subdivision of the dispersed particles. Various methods have been developed to quantify or qualify the level of filler dispersion within compounded rubber, however, these methods are currently either too burdensome and time consuming or do not provide the degree of quantification or qualification of filler dispersion that is desired.

In the known automatic microscope electronic data accumulator (AMEDA) process filled polymer specimens are hardened overnight with molten sulfur, and are polished with different grinding agents to produce a mirror-like surface. Light is reflected off the specimen surface, and the filler agglomerates, typically carbon black, are detected by their higher light reflectance as compared to reflectance off of the polymer matrix. By moving the specimen at a fixed rate, an X-Y scan of the surface is provided, and optical density differences between the filler agglomerates and the polymer matrix are used to calculate percent carbon black dispersion. However, as mentioned, the specimens must be hardened overnight, and, additionally, the different grinding/polishing steps are unduly labor intensive.

Filler dispersion has also been quantified by measuring with a light microscope the percentage area covered by black agglomerates in microtome sections of the compounded polymer. Indeed, this method is described under ASTM D2663, test Method B, entitled "agglomerate count," and, thus, serves as a standard test method for measuring filler dispersion, particularly carbon black dispersion, in polymer. In this method, the compounded rubber is microtomed into sections that are sufficiently thin to permit observation of the carbon agglomerates by transmitted light. The total cross-sectional area of all agglomerates 5 microns or larger is counted, and from the known content of carbon black in the stock, the percentage of carbon black below the 5 microns size is calculated and expressed as the percentage of carbon black dispersed. This process, however, requires freezing the compounded rubber and providing a microtome section, and, thus, is both time consuming and labor intensive.

ASTM D2663 also provides a "visual inspection" test method (test method A) and a "microroughness measurement" method (test method C). The visual inspection method generally involves tearing or cutting a polymer sample to expose a fresh surface for examination by the eye, preferably aided by a hand lens or low-power microscope. The level of dispersion is simply compared against a series of photographic standards, and, thus, provides merely a qualitative analysis of filler dispersion. The microroughness measurement method involves tracing a cut surface of a polymer specimen with a stylus to measure the amount of roughness caused by filler (carbon black) agglomerates. It is a quantitative test method, but is rather time consuming and labor intensive.

Of particular relevance to the method of the present invention is the reflected light measurement (RLM) method for measuring filler dispersion. Like the grinding/polishing method mentioned above, this method analyzes light reflected off a compounded polymer sample; however, in the RLM method, a polymer sample containing reinforcing fillers is cut by a blade, which, as it is advanced through the sample, urges the fillers to move out of the path of the cutting blade. The cut surface of the sample therefore exhibits depressions and bumps where polymer-covered fillers have been pushed ahead of the cutting blade, to either one side or the other of where the cut was made. The RLM method quantifies the level of filler dispersion by directing beams of light toward the cut surface, at an angle, such that the light beams reflected from either a depression or bump are reflected to a sensor, while light beams reflected from a smooth area of the cut surface are not picked up by the sensor. The sensor then produces an image of the reflectance from the cut surface, and this image is then compared to a standard set of images indicating dispersion ratings on a scale of 1 to 10, where 10 indicates very good dispersion. This method, while being relatively fast and requiring minimal labor, requires comparison to samples, and is therefore susceptible to error. Additionally, as filler dispersion might vary across different polymers and filler combinations, this method requires that a scale exist for the actual polymer and filler combination under study.

Andersson, Sunder, Persson and Nilsson expanded the comparative dispersion rating of the RLM method to give quantitative data as to the size and number of the disturbances (i.e. depressions and bumps) in the cut surface. See Andersson et al., Rubber World, March 1999, p.36. While such data provides some indication of dispersion, there still exists a need in the art for a less labor intensive and faster method for more accurately quantifying the level of dispersion of a filler in a compounded polymer.

SUMMARY OF THE INVENTION

In general, the present invention provides a method for determining a percent dispersion rating for fillers within a compounded polymer having a filler dispersed therein. A cut surface of the compounded polymer is prepared such that the fillers provide surface disturbances on the cut surface. Light is directed toward the cut surface, such that light incident on a surface disturbance is reflected to a sensor, and light not incident on a surface disturbance is not reflected to said sensor. From the light incident on the sensor, the percent area of the cut surface that is covered by the surface disturbances is computed, and, a percent dispersion rating is calculated as function of this percent area.

Notably, the fillers are not the surface disturbances themselves, but rather, the surface disturbances represent fillers covered by a thin layer of polymer. Surface disturbances below a certain size are considered to represent fully dispersed filler, such that, in calculating the percent dispersion rating for the filler as a function of the percent area of the cut surface that is covered by the surface disturbances, only those surface disturbances above a given selected threshold size are considered. In particular embodiments of the present invention, the percent dispersion rating is calculated according to the following equation:

$$D_{RL} \% = 100 - 100 \, U_{RF} \%/L$$

wherein $D_{RL} \%$ is the filler dispersion rating; $U_{RF} \%$ is the percent area of the cut surface that is covered by surface disturbances greater that a selected threshold; and L is the volume percentage of carbon black in the compound.

BRIEF DESCRIPTION OF THE DRAWINGS

For a complete understanding of the objects, techniques and structure of the invention, reference should be made to the following detailed description and accompanying drawings wherein.

PREFERRED EMBODIMENT FOR CARRYING OUT THE INVENTION

The present invention provides an improved method for quantifying the dispersion of fillers within a compounded polymer. This method facilitates the dispersion testing of both vulcanized and unvulcanized polymer samples, and is suitable for process and quality control testing purposes. Although not necessary, the method of this invention is preferably employed to rate the filler dispersion within a sample of compounded rubber taken from the masterbatch in a rubber manufacturing process. Also, the method herein advantageously provides a quantified dispersion rating for compounded polymers within a very short amount of time (approximately 5–15 minutes), such that the method herein can be used concurrently with common production processes, with the added benefit that, when the dispersion ratings that are calculated are out of specification, the masterbatch can be held and/or adjusted before additional processing.

Figure 1:
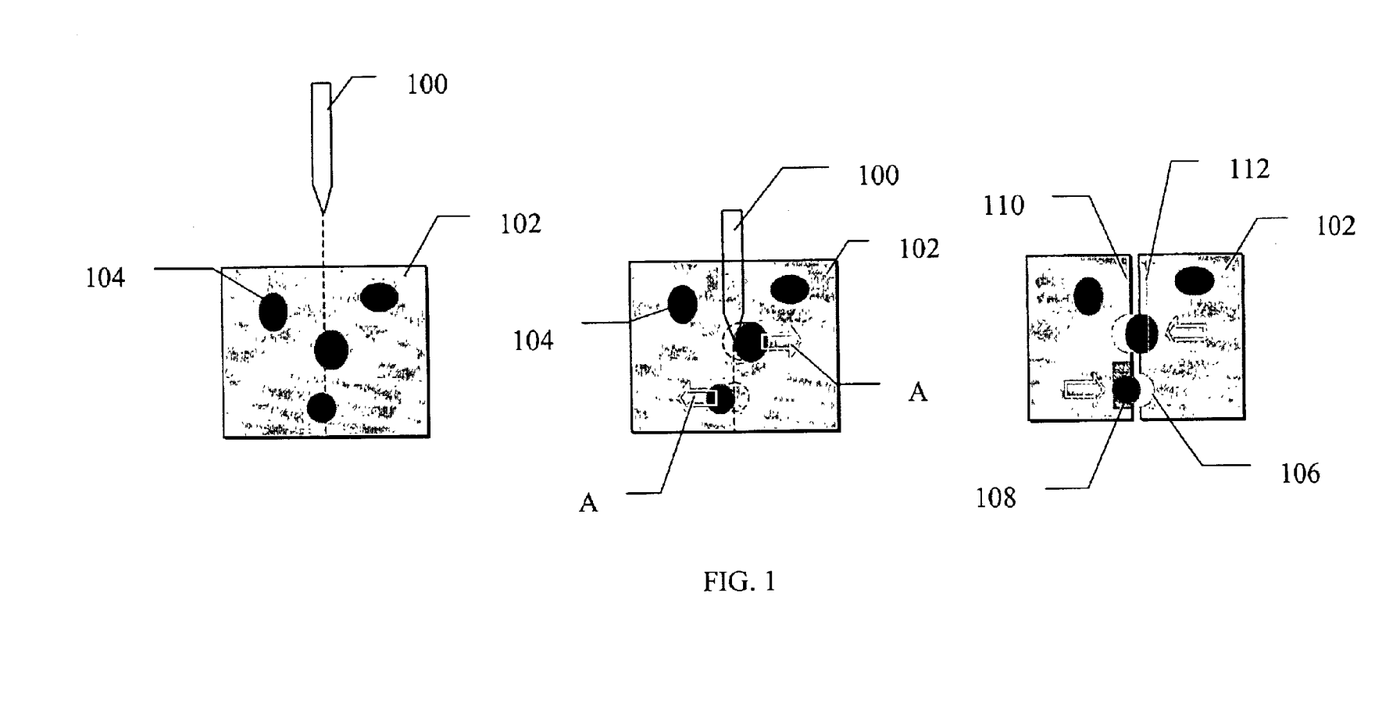
FIG. 1 generally represents the preparation of cut surface in a compounded polymer sample for the purpose of measuring the dispersion of fillers therein through the reflected light measurement method.

As mentioned, the present method focuses upon the reflected light measurement (RLM) method for analyzing the dispersion of fillers throughout a sample of compounded polymer. This method will generally be appreciated with reference to FIGS. 1 and 2. FIG. 1 shows the cutting operation of a cutting blade 100 on a compounded polymer sample 102 containing reinforcing fillers 104. As the cutting blade 100 is advanced through the sample 102, the resilient nature of the polymer deflects and shields the polymer as the blade passes through its cutting plane, and the fillers 104 are forced to move out of the path of the cutting blade 100. This movement is represented by arrows A. Movement of the fillers 104 leaves behind either depressions 106 or bumps 108 on the cut surfaces 110, 112 of the sample 102. With additional reference to FIG. 4, it can be seen that the cutting action does not expose actual filler agglomerates, but rather, the surface disturbances (106, 108) represent filler agglomerates covered by a thin layer of polymer. The surface roughness resulting from the depressions 106 and bumps 108 thus relate to the level of filler dispersion, and the RLM method can be employed to measure the level of filler dispersion within the compounded polymer composition that provided the polymer sample 102.

Figure 2:
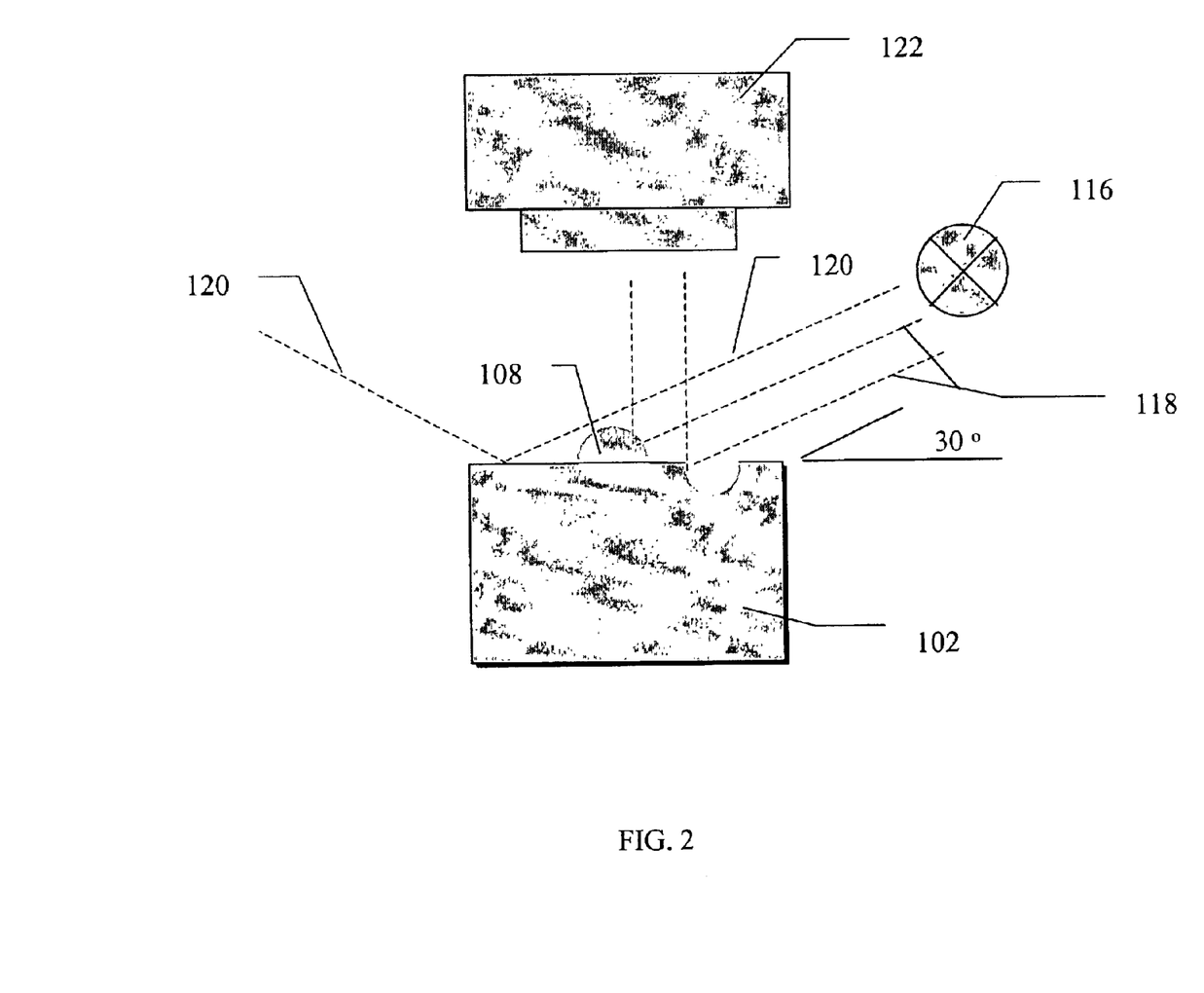
FIG. 2 generally represents the reflected light measurement method for measuring the dispersion of fillers in a compounded polymer sample.

The way in which the RLM method operates to quantify the level of filler dispersion within compounded polymer is generally depicted in FIG. 2. Therein, a light source 116 emits beams of light 118, 120 toward the cut surface 110 of a polymer sample 102 that has been cut as generally shown with reference to FIG. 1. The light beams 118 hit the cut surface 110 on a angle such that, when the light beams 118 reflect from either an indentation 106 or bump 108, the light 118 is reflected into a sensor 122, and, when light beams 120 are reflected from a smooth surface uncut surface 110, the reflected light is not picked up by sensor 122.

Figure 3:
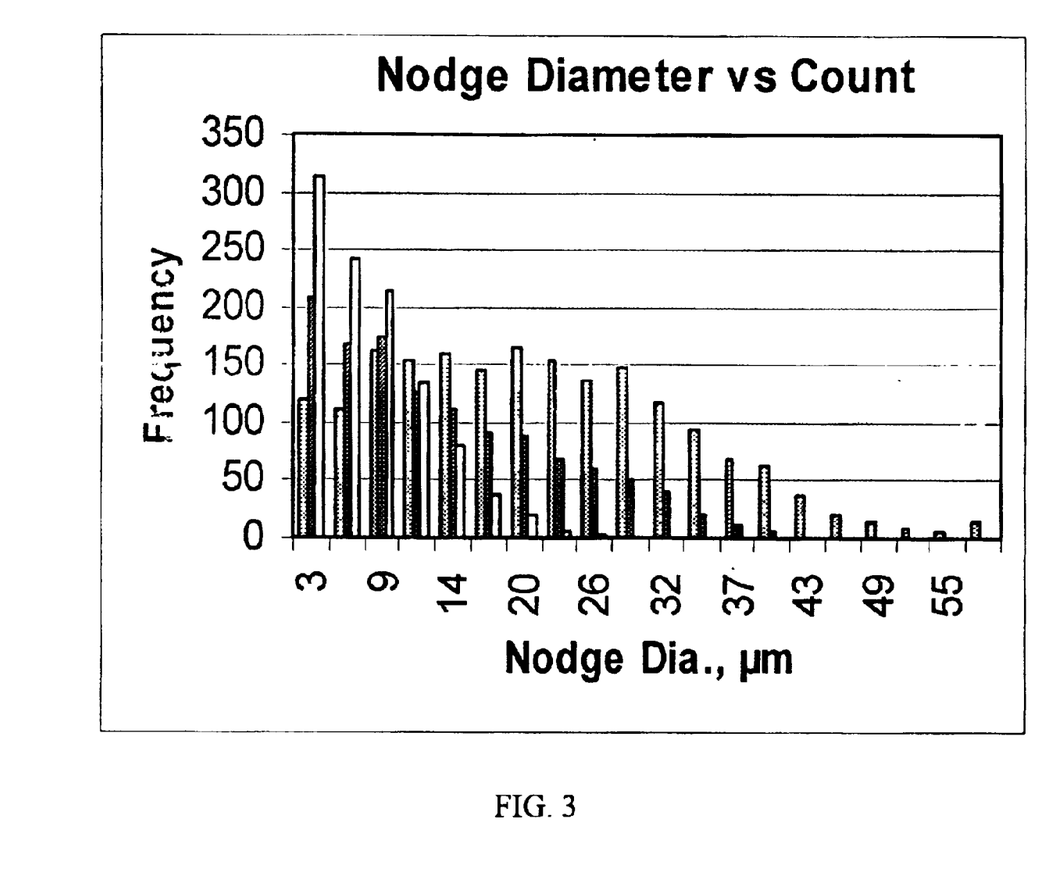
FIG. 3 is a plot of the frequency (count) of surface disturbances (nodges) versus nodge diameter, and FIG. 4 visually represents the concept that the surface disturbances on a cut sample according to this invention are not actually exposed filler agglomerates, but are rather agglomerates that are covered by a thin layer of polymer.

Light reflected back to sensor 122 thus indicates the existence of surface roughness, more particularly, the existence of filler agglomerates 104 lying across the plane through which cutting blade 100 was advanced. In order to ensure that the results obtained from the RLM method are accurate and reliable, the cut surface 110 of the sample 102 preferably includes a minimal of cut marks or smear marks from the cutting blade 100, and minimal depressions resulting from entrapped air within the polymer sample. Thus, a process for preparing the cut surface, such as that disclosed in copending application Ser. Nos. 09/978,509, entitled "Method for Preparing a Cut Surface In Uncured Rubber Samples For Measuring Filler Dispersion," is preferably employed, although not mandated. The copending application is incorporated herein by reference. Using known image processing techniques, the diameter and frequency of the surface disturbances can be measured. Such information may then be provided in chart form, as shown in FIG. 3.

Figure 4:
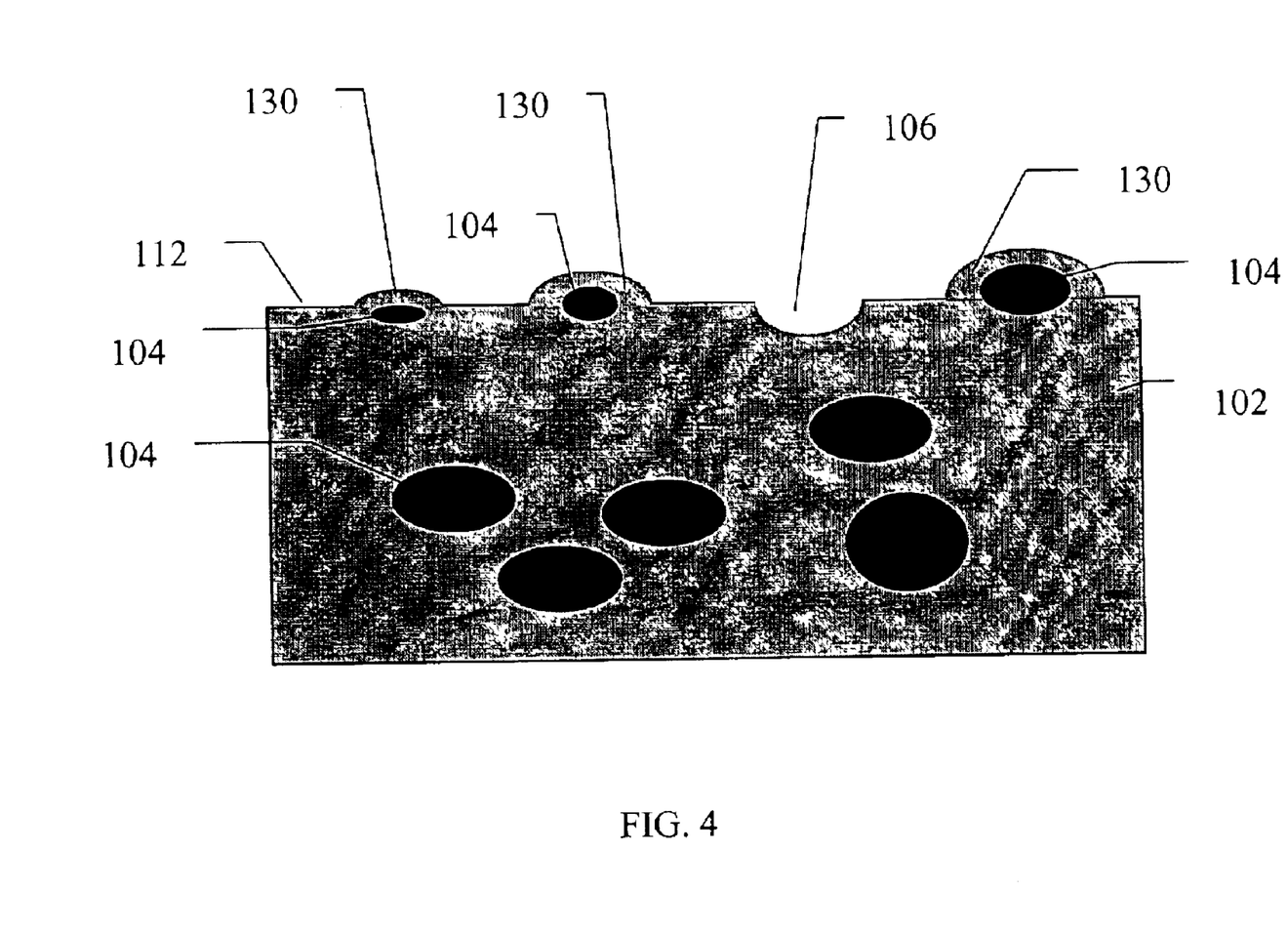

Notably, the surface disturbances (i.e., depressions 106 and bumps 108) relate to the agglomerates present in the sample, and the light beams 118 do not reflect off the surface of the filler agglomerates 104, but rather reflect off of a thin layer of polymer covering the agglomerates. This thin layer of polymer is shown in FIG. 4 by the numeral 130.

Also, it should be appreciated that only those filler agglomerates of a particular size are of interest in determining the level of dispersion of the filler, because filler agglomerates 104 below a certain threshold size are considered to represent fully dispersed filler. Thus, when considering surface disturbances, the surface disturbance size of interest will be of a size even greater than the threshold size of the filler agglomerates 104, due to the additional size added to depressions 106 and bumps 108, by the thin layer of polymer covering agglomerates 104.

The threshold size for a surface disturbance is determined experimentally as a function of both the polymer and filler.

These surface disturbances will be referred to as "nodges" to differentiate them from actual filler agglomerates 104. As mentioned, the diameter and frequency of the surface disturbances are measured through the RLM method using image processing, and this data is presented in histogram form of frequency versus nodge diameter, as shown in FIG. 3. Notably, in FIG. 3, three different duration of mixing time are depicted, and it can be seen that, as mixing time increases the mean nodge diameter decreases and the frequency of the nodges of smaller diameter increases. It will be appreciated that this is a result of the continued dispersion of the filler resulting from longer mixing times.

With the data available from the histogram one can look at specific size nodges and determine additional information regarding the compound's dispersion. Rather than a comparative rating judged against various reference scales, it would be an improvement to have a more definitive measure of the compound's dispersion. To consider this, consideration may be given to the method developed by Leigh-Dugmore, Rubber Chem. and Technology, 29, pp. 1303–1308, (1956), and specified in ASTM D2663, "Standard Test Methods For Carbon Black Dispersion", 09.01, American Society for Testing and Materials, West Conshohocken, Pa., pp. 401–411 (2001).

The basis of the Leigh-Dugmore method is that a specimen is microtome and examined under a light microscope at 70 to 100× magnification. The number of agglomerates, U, that fill a field of 10,000 graticule squares is compared to the volume percentage of the carbon black, L, in the compound. The percent of dispersed carbon black is:

$$Dispersion, \%=100-SU/L \qquad (1)$$

Wherein U is the number of graticule squares that are at least half filled with carbon black; L is the volume percentage of carbon black in the compound; and S is the swelling factor of the specimen based on area.

The microtome technique requires the use of naphtha to remove the specimen from the knife edge. This results in swelling of the specimen. By measuring the specimen before and after application of the naphtha, an area swelling factor, S, can be calculated and used in the calculation above.

The ASTM D2663, Method B, standard is explicit in using the 10,000 graticule squares for estimating the area of the filler (particularly carbon black) agglomerates. Today, image processing can make this tedious task, simple. If U % is the percent undispersed agglomerate count of carbon black, 10,000 is the total number of squares in the field and U is the number of squares half filled with agglomerates in the field, then:

$$U\% = 100(U/10,000)$$
$$= U/100$$
$$= 100 \, U\%$$

Substituting into (1), $$D\%, Dipersion, \% = 100 - S(100 \, U\%/L) \qquad (2)$$
$$= 100 - 100S \, U\%/L$$

It is important that ASTM D2663 states that the count of U encompasses agglomerates down to about 5 μm. It is assumed here that any carbon black agglomerate smaller than this threshold represents fully dispersed carbon black. Image processing then would necessitate that the area calculated for U % exclude any contribution from agglomerates less than this threshold.

Medalia, Rubber Chem. and Technology, 34, p. 1134–40 (1961), comments that the Leigh-Dugmore calculation assumes that the carbon black agglomerate is composed of solid carbon just as are the fully dispersed aggregates. According to Medalia, however, the volume of carbon black in the agglomerate may vary according to several factors including the bulk density of the black, compression of the agglomerates during mixing, and the presence of oils and polymers in the agglomerates.

Medalia also notes that since the agglomerates are not 100% carbon, they may swell with the application of naphtha. He revised the Leigh-Dugmore calculation for a new dispersion rating, Dn, as follows:

$$Dn, Dispersion, \%=100-vUS/AL \qquad (3),$$

wherein v is the average volume fraction of carbon black in the agglomerate; and A is the area swelling factor of the agglomerate. The importance of this lies in the fact that the Leigh-Dugmore calculation may result in negative percent dispersion ratings. If the calculation of Medalia is applied, the actual percent dispersion will always be greater than that calculated by Leigh-Dugmore.

To apply these calculations to the reflected light data, we consider the histogram data (e.g., FIG. 3) and the method for determining the nodge count. The nodge size and count are determined by optical image analysis of a freshly cut surface, as disclosed above. As the specimen is cut the underlying agglomerates are pushed to one side or another resulting in depressions and bumps on the cut surface. The resulting depression or bump represents an agglomerate under the surface of the cut. The nodge diameter that is calculated from these surfaces is larger than the underlying agglomerate (FIG. 4). This is important, since if one applies either calculation (1), (2) or (3) above, there must first be some method for disregarding small agglomerates (those less than 5 μm) or disregarding small nodges that are covering the agglomerates.

Given the histogram data, the area represented by the nodges is easily determined from the radius and frequency for all nodges greater than the determined nodge threshold. Then knowing the scan area, the percent nodge area, $U_{RF}$ %, can be determined by computing the sum of the surface area covered by all nodges having a diameter greater than the threshold, and dividing this sum by the total area of the cut surface (or the total scanned area) and multiplying by 100, to obtain a percent value. In calculating the area, the surface area covered by the nodges is assumed to be circular, as is generally practiced in the art, and area thus equals pi times the square of the radius of the nodge ($\pi^2$). $U_{RF}$ %, the percent area of the cut surface that is covered by the surface disturbances greater than the threshold, is employed in the equation (2), calculated above, such that filler dispersion is expressed by the following equation:

$$D_{RL} \%=100-100S \, U_{RL} \%/L \qquad (4)$$

wherein $D_{RL}$ % is the filler dispersion rating; S is 1 (because no solvent is required in the present process); $U_{RF}$ % is the percent area of the cut surface that is covered by surface disturbances greater that the threshold; and L is the volume percentage of carbon black in the compound. Notably, the average volume fraction of carbon black in the agglomerate, "v" in equation (3), might also be incorporated into equation (4).

Experimental

The purpose of the following experiment is to determine if a correlation exists between the ASTM D2663, method B, transmitted light technique and the reflected light technique described, and to present examples of the new calculation.

The formulae and mixing procedures are summarized in Tables I through IV. Here testing was performed with unvulcanized samples since only masterbatches were studied. Four additional compounds with different fillers, polymers and loadings were also evaluated to determine the relative effect of the new dispersion rating to the optical comparison method. These tests were done on vulcanized samples.

TABLE I

Formulation for Compound TPI

| INGREDIENT | PHR |
| --- | --- |
| SMR 5 | 100.0 |
| N330 Black | 45.0 |
| 6 PPD | 1.5 |
| TMQ | 1.5 |
| Stearic Acid | 2.0 |
| Zinc Oxide | 3.0 |

TABLE II

Mixing Variations

| Batch Number | Rubber Break Down, min | Filler Mix Time, min. | Total Mix Time, min. |
| --- | --- | --- | --- |
| A1 | 1 | 5 | 6 |
| A2 | 1 | 6 | 7 |
| A3 | 1 | 7 | 8 |
| A4 | 1 | 8 | 9 |
| A5 | 1 | 9 | 10 |
| A6 | 1 | 11 | 12 |
| A7 | 1 | 13 | 14 |
| A8 | 7 | 11 | 18 |

TABLE III

Batch Weights

| INGREDIENT | PHR | Batch Weight |
| --- | --- | --- |
| Masterbatch | | |
| SMR 5 | 100.0 | 840.0 |
| N330 Black | 45.0 | 378.0 |
| 6 PPD | 1.5 | 12.6 |
| TMQ | 1.5 | 12.6 |
| Stearic Acid | 2.0 | 16.8 |
| Zinc Oxide | 3.0 | 25.2 |
| Masterbatch total | 153.0 | 1285.2 |

TABLE IV

Mixing Procedure

| Mixing Event | Occurs at: |
| --- | --- |
| Masterbatch: | |
| Rubber breakdown | Time variable according to Table II |
| Filler and misc ingredient mix time | Time variable according to Table II |
| Sweep at: | 2.5, 3.75, 5.5 and 8 minutes where applicable |
| Drop batch at: | Total Time according to Table II |

The following instruments, equipment and procedures were used:

Dispersion Rating (DR): The DR was measured using the TECH PRO, INC. dispergrader 1000NT. Magnification level was 100 and the comparative dispersion rating scale selected was the RCB scale. Samples were cut using the special apparatus described in copending Ser. No. 09/978,509, already incorporated herein.

Dispersion Histogram: The histogram of nodges versus count is automatically provided by the dispergrader 1000NT. The measurement accuracy is 3 µm. Twenty cells were selected to be displayed in the histogram from 3 to 57 µm. This histogram is generated on the same data set as used to calculate the DR above.

Dispersion, %: The dispersion percent was measured according to ASTM D2663, Method B, using a Southern Precision Stereo Microscope with Polaroid BMC camera and Sigma Scan Image processing software. Specimens were analyzed at 100× magnification.

Internal Mixer: All batches were mixed in a Farrel laboratory internal mixer, size B. The nominal volume is 1.5 liters with a fixed rotor speed of 77 rpm.

All 8 batches were analyzed using the automatic dispersion rating and histogram data. Four batches were analyzed according to ASTM D2663, Method B.

Results and Discussion

The test results are shown in tables V and VI.

To determine the nodge threshold that best represents the undispersed agglomerate data, the results of the histogram data were sued to calculate the percent nodge area, $U_{RF}$ %, for 4 different threshold values. These values were the total areas for all nodges greater that 17, 20, 23 and 26 µm respectively. These values were used to calculate the reflected light dispersion percentage, according to calculation (2), and the results are given in Table V. The results from 3 measurements using ASTM D2663, Method B, are also presented. It can be seen that $D_{RL1}$ at the 20 µm threshold relates relatively well with the Leigh-Dugmore calculation.

TABLE V

Experimental Results
Comparison of Reflected Light Dispersion to ASTM D2663, B

| BATCH NUMBER | DRL1, % Threshold >17 | DRL1, % Threshold >20 | DRL1, % Threshold >23 | DRL1, % Threshold >26 | ASTM D2663, B D, % |
| --- | --- | --- | --- | --- | --- |
| A1 | −18.4 | −10.7 | −1.3 | 9.5 | 1.1 |
| A2 | 21.1 | 27.7 | 36.3 | 47.2 | |
| A3 | 61.1 | 67.0 | 73.8 | 81.3 | |
| A4 | 72.0 | 76.1 | 80.2 | 84.9 | 75.4 |
| A5 | 80.1 | 83.1 | 86.3 | 90.0 | |
| A6 | 90.5 | 92.2 | 93.6 | 94.9 | |
| A7 | 96.2 | 97.1 | 97.7 | 98.3 | |
| A8 | 98.2 | 99.1 | 99.5 | 99.8 | 99.3 |

The value $D_{RL1}$ is negative for batch A1 until the 23 µm threshold is reached. This was one of the problems addressed by Medalia. In consideration of these very low numbers, he states that "such stocks are readily recognized as being of inadequate dispersion" and the exact value "would not have any practical value". Likewise, ASTM D2663 suggests that negative dispersion ratings are "extremely poor" and can be reported as "0" or "no dispersion".

It is also seen from the results in TABLE V that, as the mixing times are increased, the dispersion ratings, DRLI, become closer and closer between the different threshold levels. It might be suggested that in most normal mixing operations, these values would be in the 70% or greater range, making the exact choice of threshold value less significant.

The opportunity now exists to apply Medalia's revised calculation. The swelling factors S and A, in calculation (3) need not be considered since the reflected light method does not use a solvent. However, the volume of black in the agglomerate is still not known. Medalia recommends in his discussion of the revised Leigh-Dugmore calculation that the original calculation that is used in the ASTM method be retained since the values of v and A were indeterminate. The modified Leigh-Dugmore calculations may be used although v is still indeterminate, and it is considered worthwhile to investigate Medalia's revised calculation in the future. Medalia further suggests that the Leigh-Dugmore calculation of percent dispersion be considered more meaningfully as relative rather than accurate values of percent dispersion.

One of the difficulties of using the "fixed scale" method of optical comparison is that there is no consideration for the loading of black in the compound. Although this does not present a problem comparatively, it is problematic conceptually. The original automatic dispersion ratings, DR, are shown in Table IV. Here the ratings go from nearly −4.0 to +9.0. This, when viewed as a relative scale, gives good resolution between the samples. When looking at obviously bad to obviously good samples, this quantification is easy to understand. If, however, only two samples were tested, for example A4 and A5 with DRs of 2.6 and 3.9, it would be difficult to know what these results meant on a more absolute scale.

TABLE VI

Experimental Results
Automatic Dispersion Rating for Mixing Study
RCB Scale

| BATCH NUMBER | DISPERSION RATING, DR |
|---|---|
| A1 | −3.94 |
| A2 | −1.62 |
| A3 | 2.20 |
| A4 | 2.61 |
| A5 | 3.89 |
| A6 | 6.26 |
| A7 | 7.92 |
| A8 | 9.15 |

If samples A4 and A5 are looked at using the reflected light dispersion rating, $D_{RL1}$, the values of 80.2 and 86.6 (23 μm threshold) are in a range of more comprehendible significance. It is possible for $D_{RL1}$ to be negative but the maximum value is 100. These $D_{RL1}$ values, while they may not be exact percent dispersion ratings, certainly reflect the relative closeness of the dispersion to the maximum.

To apply the new dispersion rating to an unknown set of samples, 4 additional compounds were examined. The polymer type, filler type and loading are shown in Table VII and the results of the tests in Table VIII.

TABLE VII

Experimental Results
Additional Compound Description

| Compound | Polymer Type | Filler Type | Total Formula phr | % Volume of Filler, L |
|---|---|---|---|---|
| B1 | CR | CB | 220 | 20.1 |
| B2 | EPDM | CB, Whiting | 371 | 20.0 |
| B3 | EPDM | CB, Clay | 340 | 17.0 |
| B4 | SBR | CB, Whiting, Silica | 270 | 23.8 |

TABLE VIII

Experimental Results
Optical Comparison versus DRL1, %, Reflected Light
Dispersion % for Additional Compounds

| Compound | DR R CB Scale | DRL1, % Threshold >23 |
|---|---|---|
| B1 | 3.39 | 73.0 |
| B2 | 1.82 | 76.8 |
| B3 | 4.83 | 84.5 |
| B4 | 0.17 | 42.8 |

The four compounds, B1 to B4, are ordinary production mixes. The physical properties meet the requirements of the compound and it is assumed that the materials are mixed sufficiently. Therefore, the dispersion rating and the % dispersion on a relative scale represents acceptable dispersion.

The results from the sample B1 to B4 may help show the application of $D_{RL1}$. First, as stated by Medalia, the true percent dispersion is greater than that as determined by the Leigh-Dugmore calculation. Next we look at the process of dispersion defined as breaking down filler agglomerates to their ultimate size, and we see that the threshold of 5 μm as stated by ASTM D2663, is really based on carbon black filler dispersion. The threshold for clay and whiting would necessarily be different and probably higher since the particle sizes of these fillers are significantly larger than carbon black. Finally, we can see that both DR and $D_{RL1}$ give relative data about filler dispersion. The $D_{RL1}$, however, leads us to a more objective view of the state of dispersion.

The histogram data affords us the opportunity to further investigate the use of the reflected light percent dispersion rating. These include studying a broader range of compounds with carbon black, comparison to other standard methods and the affect of other fillers.

The reflected light method for measuring the roughness of a cut surface has been shown to provide a fast economical and definitive measure of dispersion. Because the surface roughness is dependent on not only dispersion, but also polymers, fillers and filler loadings, different scales for image processing of the variety of compounds to be analyzed may be required, but readily generated.

These scales provide a good relative measure of dispersion. It would also be helpful to know, even on a relative basis, an approximate percent dispersion. By applying a modified Leigh-Dugmore calculation to the histogram data obtained from the reflected light method, a relative percent dispersion was obtained. These results relate well with the values obtained when applying the Leigh-Dugmore calculation and further provide detailed dispersion information in a fast and quantitative measurement. The method provides a more universal scale for measuring dispersion and is equally applicable to vulcanized and unvulcanized specimens.

Fundamentally, this invention contemplates the preparation of a cut surface of a polymer compounded with fillers, while leaving dispersed filler agglomerates substantially undisturbed and evidenced by surface disturbances (in the form of depressions or bumps), which represent the presence of such agglomerates. The areas of these surface disturbances that exceed a selected threshold are then summed, and that summation is indicative of undispersed filler in the sample plane. The percent of the summation area to the total area of the plane is then indicative of the percent of undispersed filler, which can be employed to calculate a dispersion rating (%) from the known volume percent of the filler in the compounded polymer under study.

In light of the foregoing, it should thus be evident that the process of the present invention, providing an improved method for calculating surface roughness to indicate filler dispersion, substantially improves the art. While, in accordance with the patent statutes, only the preferred embodiments of the present invention have been described in detail hereinabove, the present invention is not to be limited thereto or thereby. Rather, the scope of the invention shall include all modifications and variations that fall within the scope of the attached claims.

What is claimed is:

1. A method for determining a percent dispersion rating for fillers within a compounded polymer comprising the steps of:

preparing a cut surface of a compounded polymer having a filler dispersed therein, wherein the fillers provide surface disturbances on the cut surface;

directing light toward the cut surface such that light incident on a surface disturbance is reflected to a sensor and light not incident on a surface disturbance is not reflected to said sensor;

computing, from the light incident on said sensor, the percent area of the cut surface that is covered by the surface disturbances; and calculating the percent dispersion rating for the filler as a function of said percent area.

2. The method of claim 1, wherein the percent dispersion rating is calculated according to the following equation:

$$D_{RL}\% = 100 - 100\, U_{RL}\%/L \qquad (4)$$

wherein $D_{RL}\%$ is the filler dispersion rating; $U_{RF}\%$ is the percent area of the cut surface that is covered by surface disturbances; and L is the volume percentage of carbon black in the compound.

3. The method of claim 1, wherein, is said step of computing the percent area of the cut surface that is covered by the surface disturbances, only those surface disturbances above a selected threshold size are considered.

* * * * *

UNITED STATES PATENT AND TRADEMARK OFFICE
CERTIFICATE OF CORRECTION

PATENT NO. : 6,775,004 B1 Page 1 of 1
APPLICATION NO. : 10/266411
DATED : August 10, 2004
INVENTOR(S) : John B. Putman It is certified that error appears in the above-identified patent and that said Letters Patent is hereby corrected as shown below:

On the title page item (76), should read: John B. Putman, 1810 Highbridge Rd., Cuyahoga Falls, OH (US) 44223

Matthew C. Putman, 441 Graham Rd., Apt. 4, Cuyahoga Falls, OH (US) 44223

Signed and Sealed this

Twenty-sixth Day of February, 2008

JON W. DUDAS
*Director of the United States Patent and Trademark Office*